United States Patent [19]

Keates et al.

[11] Patent Number: 5,171,319
[45] Date of Patent: Dec. 15, 1992

[54] FOLDABLE INTRAOCULAR LENS SYSTEM

[76] Inventors: Richard H. Keates, 613 Nyes Pl., Laguna Beach, Calif. 92651; Richard T. Schneider, 17 Alachua Highlands, Alachua, Fla. 32615

[21] Appl. No.: 832,970

[22] Filed: Feb. 10, 1992

[51] Int. Cl.⁵ ............................................ A61F 2/16
[52] U.S. Cl. ...................................... 623/6; 606/107
[58] Field of Search ........................... 623/6; 606/107

[56] References Cited

U.S. PATENT DOCUMENTS

| | | | |
|---|---|---|---|
| 4,657,546 | 4/1987 | Shearing | 623/6 |
| 4,753,653 | 6/1988 | Bissonette et al. | 623/6 |
| 4,759,763 | 7/1988 | Bissonette et al. | 623/6 |
| 4,834,754 | 5/1989 | Shearing | 623/6 |
| 4,844,065 | 7/1989 | Faulkner | 128/321 |
| 4,878,912 | 11/1989 | Castleman | 623/6 |
| 4,911,714 | 3/1990 | Poley | 623/6 |
| 4,917,680 | 4/1990 | Poley | 623/6 |
| 4,957,505 | 9/1990 | McDonald | 623/6 |
| 4,959,070 | 9/1990 | McDonald | 623/6 |
| 4,976,716 | 12/1990 | Cumming | 606/107 |

Primary Examiner—Randy C. Shay
Attorney, Agent, or Firm—Poms, Smith, Lande & Rose

[57] ABSTRACT

A foldable IOL system includes a foldable bi- or multi-focal IOL and lens insertion instrument capable of unfolding the IOL by externally applied forces. The foldable IOL includes an oval lens body equipped with haptic structures for fixing the lens body within one of the chambers of the human eye. The lens body is foldable along two slits placed in the lens body parallel to and on either side of the oval lens body's long axis. The lens body is divided by the two separations into three parts: A central part and two side parts. The central part may be divided into two or more areas endowed with different optical powers. The lens body may be surrounded by an elastic ring that will keep the unfolded IOL in its unfolded position. The lens body may also have locking pins inside the slits that will keep the IOL in its unfolded position. The lens insertion instrument includes shielding to protect the folded IOL from loose tissue particles during the insertion process. Also provided is a vice-like holder for the central portion of the IOL to provide a stable base against which the two side parts may be unfolded. Folding and unfolding is aided by spring-activated platforms and threads that may be wound or unwound around a retaining drum. The lens folding and unfolding sequence and the removal of the insertion instrument's shielding may be mechanized through the use of linear and rotary hydraulic actuators.

28 Claims, 5 Drawing Sheets

FOLDABLE INTRAOCULAR LENS SYSTEM

FIELD OF THE INVENTION

The present invention relates to foldable intracular lens systems and more particularly to bifocal foldable intraocular lenses and lens insertion devices which allow insertion of a lens into one of the chambers of the human eye through incisions sufficiently small so as not to require stitches.

BACKGROUND OF THE INVENTION

Many different types of intraocular lens (IOL) structures are presently in use. Such devices have been developed to satisfy the need for an artificial lens to be implanted into one of the chambers of the human eye once the eye's natural lens has been removed because it became useless due to the formation of a cataract.

While such IOLs and the procedures for inserting IOLs have proven to be very beneficial for patients afflicted with cataracts, there remains a need for improvement in several areas.

First, unlike the eye's natural lens, the artificial IOL lens is incapable of accommodation. Therefore, the patient will experience sharp vision for only one distance, usually chosen to be a far distance, for example 100 meters. Reading is therefore not possible unless the patient wears reading glasses. It is therefore desirable to provide a bifocal IOL, allowing the patient to switch between reading and distance vision instantly, thereby avoiding the need to remove or put on glasses each time a change in viewing is made.

Second, there is a need to reduce to a minimum trauma caused by the cataract operation, since people afflicted with this disease are typically of advanced age. It is highly desirable to keep the size of the incision, and therefore the size of the resulting tunnel into the eye, to a minimum. Typically, this incision should be on the order of 3.5 mm or less. Keeping within this size restriction allows the surgeon to forego suturing of the wound and provides for faster healing with a minimum of associated pain. Since the size of the body of typical IOLs is 6 mm or more, it is necessary to find ways to fold such IOLs so they can be passed through an approximately 3 mm tunnel.

Flexible and foldable IOLs and bifocal IOLs are known in the art. A flexible IOL is described by Mazzocco (U.S. Pat. No. 4,573,998). A flexible IOL holder is described by Keates (U.S. Pat. No. 4,619,657) and a foldable bifocal IOL is described by Bissonnette (U.S. Pat. No. 4,753,653). The Mazzocco patent teaches that the optically active areas of the IOL are manufactured from an elastic material displaying an elastic memory. Since the typical IOL is larger by a factor of about 2 than the desired incision, the Mazzocco patent teaches that the IOL is to be reduced in size by a factor of at least 2 and by as much as 80% by deforming the elastic material with mechanical forces. This requires not only a material compatible with the eye's tissue, but a highly elastic material as well.

Those familiar with elasticity theory will realize that, in accordance with Hooke's law, upon a certain limit of deformation the material will "flow," meaning upon release of the applied mechanical force the material will not return to its original shape. Material deformation to the extent required to roll a circular IOL disc into a cylindrical shape poses the danger that some of the material at certain locations on the IOL will be more deformed than the material at other locations. Therefore, some parts of the IOL may be stressed past their elastic limit and exhibit flow, while the material at other locations will stay below this limit and exhibit no flow. Consequently, prior art flexible and foldable IOLs present a danger for distortion of the optically active areas of the IOL, thereby severely influencing the performance of the IOL. Further, in part because of such flow problems, the number of materials suitable for use in forming IOLs is limited. One candidate material for such use is silicon. However, this material has lately shown adverse effects on human tissues, and in particular in connection with the use of silicon as breast implants, and it remains to be seen what the long term effects of this material will be to eye tissues.

Several attempts have been made to overcome these problems. For example, the Keates and Bissonette patents both describe a bifocal foldable IOL employing the widely tested material PMMA. Also, both patents refrain from distorting or deforming by mechanical forces the optically active areas of the IOL. The Keates patent describes a flexible lens holder, whereby relatively rigid PMMA lenses are inserted into pockets, thus allowing the lens/lens holder assembly to be folded and inserted into one of the chambers of the human eye through the above-described tunnel. Unfolding of the assembly inside the eye is accomplished by the lens holder. The Bissonette patent describes two half-moon shaped rigid IOLs that are connected by hinges. The two half moons are folded onto each other, thus reducing the size of the assembly by a factor of two. Upon insertion through the tunnel, the hinges facilitate unfolding inside the eye.

However, the technologies taught by Keates and Bissonette suffer from several common problems. First, if unfolding of a lens within the eye is not carried out to extreme precision, double images will result. In attempting to overcome this problem, Keates uses a rigid material endowed with memory and placed inside the peripheral ring of its lens holder, while Bissonette relies on the elastic properties of its hinges to insure proper unfolding. A problem with the Bissonette approach, however, is that the hinges provide little leverage, thus requiring additional externally applied force to unfold the lens. More specifically, since the edges of the lens will touch tissue upon partial unfolding, and since this tissue, or the IOL itself, has to be displaced to allow full unfolding, it is seen that significant forces are required to accomplish full unfolding. Such forces would have to be applied with the hinges being in a poorly leveraged position. Further, loose tissue particles picked up during the move through the tunnel can lodge in the area connecting the two lens halves, thus making total unfolding impossible.

Alternatively, to facilitate unfolding, Keates uses an elastic material in a better leveraged location than the Bissonette patent. However, this still may not provide the precision required to avoid double images. In an alternative embodiment, Keates has its elastic material inserted by the surgeon after partial unfolding has already taken place so as to insure full unfolding. However, this approach may not be popular with surgeons.

Another problem exhibited by prior art foldable IOLs such as those disclosed by Keates and Bissonette is that the area directly on the lens' optical axis cannot be used due to the split running through this area which is required to make folding possible. From an optical point of view, this area is prime real estate and should not be abandoned. Bifocal IOLs have an inherent real estate problem. As their name implies, the bifocal lens creates two images, one for reading and one for distance. Unlike bifocal spectacles, in a bifocal IOL both parts of the lens are always in use regardless of whether the patient wishes to read or view for distance. Since the two images created by the two lens parts are superimposed, one of the two images must always be out of focus. The unsharp image has to be removed by the brain's image evaluation system. For this reason, all bifocal IOLs have a smaller useful area than a single power IOL. In addition, light rays coming from areas at the periphery of the lens create images of reduced quality, while the central part of the lens produces images of highest quality. This central part of the lens is therefore called "prime real estate." In a bifocal IOL this prime real estate should not be abandoned.

Thus, a need exists for a foldable bifocal IOL that does not require large elastic distortion of its optically active areas upon insertion in the human eye, that does not abandon prime real estate and that can be unfolded to a degree of precision sufficient to avoid formation of double images.

SUMMARY OF THE INVENTION

Accordingly, a principal object of the present invention is to provide a foldable bifocal or multi-focal IOL system that does not require a large elastic distortion of its optically active areas upon insertion in the human eye.

A further object of the present invention is to provide a foldable bifocal or multi-focal IOL system that does not abandon the lens' prime real estate.

Yet another object of the present invention is to provide a foldable bifocal or multi-focal IOL system that can be unfolded with a degree of precision sufficient to avoid formation of double images. In accomplishing these and other objects, there is provided a foldable bifocal IOL system comprising a foldable bifocal IOL lens and an insertion instrument capable of unfolding the IOL lens by externally applied forces. The foldable bifocal IOL lens comprises an oval lens body equipped with haptic structures for fixing the lens body within one of the chambers of the human eye. The lens body is made of a rigid lens material such as PMMA, acrylic or other material compatible with human eye tissue. The oval lens body measures typically 6 mm on its larger axis and 5 mm on its smaller axis. The lens body is foldable along two separations or slits, neither of which penetrates through prime real estate. These separations are cut into the lens body after the lens is manufactured in one piece. The cutting process is controlled so that it does not penetrate the lens body totally but leaves a small material thickness intact at the bottom of the cut. The intact material thickness is kept sufficiently thin so that the material left intact is capable of folding without experiencing breakage. Many materials, including PMMA and acrylics are capable of this. The lens body is divided by the two separations into three parts: A central part about 2 mm wide and two identical side parts. The central part may be subdivided into two or more areas endowed with different optical powers. The lens body may be surrounded by an elastic ring that will keep the unfolded IOL in its unfolded position. The lens body may also be supplied with locking pins inside the separations that will keep the IOL in its unfolded position and would require a certain force for a lock-in that is supplied and controlled by external forces delivered by the insertion instrument.

There is also provided an insertion instrument comprising shielding to protect the folded IOL from loose tissue particles while it travels through the insertion tunnel. Also provided is a vise-like holder for the central portion of the IOL to provide a stable base against which the two side parts of the IOL may be unfolded and locked into place. The unfolding of these parts is aided by two spring-activated platforms and may be initiated by unfurling two threads from around a retaining drum after the insertion instrument is properly positioned and the tunnel shields are withdrawn. Refurling of the same threads about the retaining drum may be used to refold the platforms to facilitate withdrawal of the insertion instrument from the eye.

The lens unfolding sequence may be mechanized through the use of two hydraulic linear actuators and two hydraulic rotary actuators. To facilitate sterilization, the hydraulic fluids used in these actuators is distilled water or balanced saline solution and the valves initiating the required motions are electromechanically activated through a sequence controlled by a microprocessor.

Other objects, characteristics and advantages of the present invention will become apparent from a consideration of the following detailed description with reference to the accopanying drawings.

DETAILED DESCRIPTION OF THE INVENTION

Referring now to the drawings, wherein like numerals represent like parts throughout the several views, a foldable bifocal intraocular lens 10 is shown in FIGS. 1-5. The foldable bifocal IOL 10 has a generally over lens body 12 having a longer axis of approximately 6 mm and a shorter axis of approximately of 5 mm. As will be described in greater detailed hereinbelow, an oval lens body foldable along its longer axis has an advantage over a circular lens body having a diameter equal to the oval's longer axis, in that the oval can be folded into a smaller package than the circular lens. For iris openings of 5 mm or less, the effective shape of the optical area of an oval lens body having a short axis of 5 mm would still be circular. Such a 5 mm iris opening is typical for daylight viewing. Only under very poor illumination conditions would an iris opening larger than 5 mm occur. In such a situation, an optical area of oval shape would indeed be used.

However, it can be surmised that this is not a disadvantage since nature uses oval configurations for night hunting animals such as cats. It may be theorized that light rays coming from the outer edges of the lens create images of poor quality. However, in situations of sufficient illumination, where the iris opening is small, rays going through the outer parts of the lens are blocked out by the iris. In contrast, under conditions of poor illumination, these rays are needed to obtain any image at all. Therefore, nature, through the use of an oval optical area, makes a compromise to accept poor acuity in the vertical direction while better acuity is maintained in the horizontal direction, where it is more likely that danger or prey may be located. Under well known optical principles, this works especially well if a cylinder is superimposed on the spherical surface of the cornea. Some humans indeed possess such a cylinder, which is usually referred to as an astigmatism and which is usually considered a visual deficiency. However, it is probably a remnant from the days when man had to be a nocturnal hunter, since most of the animals typically serving as man's food supply, for example deer, are in the open only at night. It is well known that patients possessing the trait of astigmatism can see well for distance and read without glasses even with a monofocal IOL.

Figures 1, 1A:
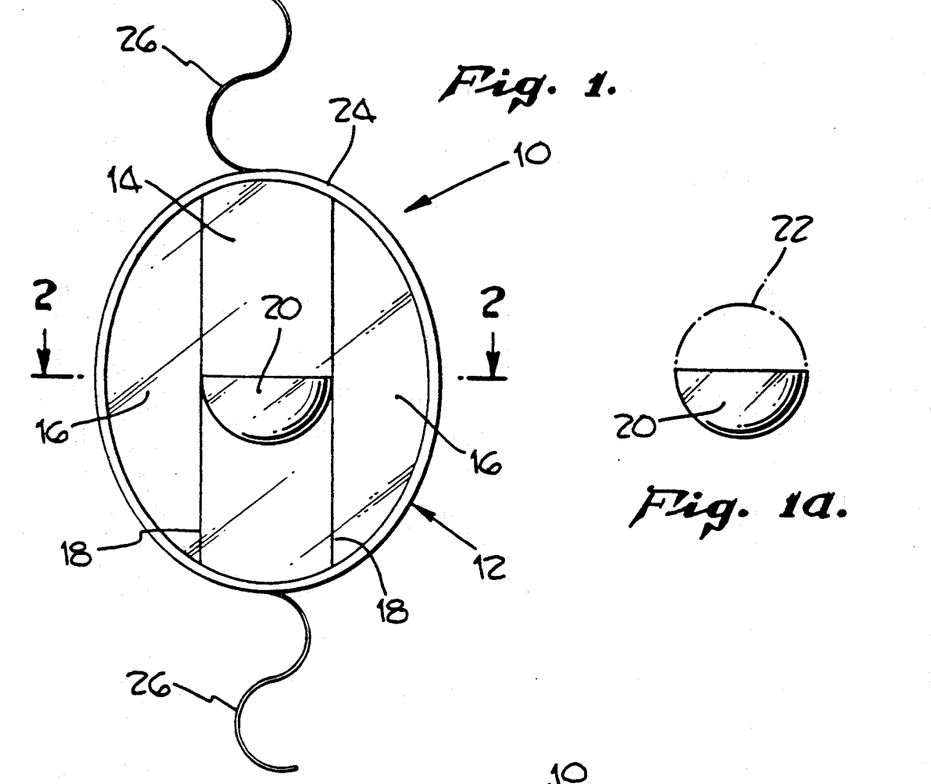
FIG. 1 is a top plan view of a bifocal foldable IOL illustrating the principles of the present invention.
FIG. 1a is a top plan view of the central portion of a multi-focal foldable IOL illustrating the principles of the present invention.

As is further seen in FIG. 1, oval lens body 12 is divided into a central segment 14 and two side segments 16 by separation cuts 18 running approximately parallel to the longer axis of oval lens body 12. Central segment 14 is approximately 2 mm wide, while side segments 16 are each approximately 1.5 mm wide at their widest point. Central segment 14 has a first semicircular subsegment which has a higher optical power than the rest of oval lens body 12. The diameter of first semicircular sub-segment 20 is approximately the same as the width of central segment 14 and is approximately coincident with the shorter axis of oval lens body 12. First semicircular sub-segment 20, with its higher optical power than the rest of oval lens body 12, is intended for reading, while the rest of oval lens body 12 is intended for distance vision. Under conditions of good illumination, which can generally be expected to exist if reading is attempted, the iris will close to approximately 2 mm thereby providing a patient with equal areas for reading and distance viewing. If the iris open wider due to less intense illumination, it is likely that the patient is in a situation where distance vision is desired, since if the patient wanted to read he would see to it that he had bright illumination. With the iris opened wider, the blurred image provided by the reading portion of oval lens body 12 (i.e., first semicircular sub-segment 20) will be of lesser intensity than the sharp image provided by the remainder of oval lens body 12. This difference in image quality will help the image evaluation system of the brain to discriminate, through the well known process of thressholding, against the blurred image caused by the reading part 20 of oval lens body 12. As seen in FIG. 1a, an alternative embodiment includes a second semicircular subsection 22, having an optical power suitable for intermediate distances (typically 1-2 meters), so that the patient can, while reading, also look at objects in close proximity without requiring the brain to change settings. Second semicircular subsection 22 has a diameter approximately the same as the width of central segment 14 and which is aligned approximately coincident with the shorter axis of oval lens body 12.

Side segments 16 and the portions of central segment 14 not included in either the first or the second semicircular sub-segment, have the same optical power, namely one that is required for distant vision. This is of course different for each patient, but 20 diopters may be considered a typical value. The optical power of first semicircular sub-segment 20 must be at least approximately 3.5 diopters larger than the optical power of the remainder of oval lens body 12. In an embodiment including second semicircular subsection 22, the optical power of that section is approximately 1.5 to 2.5 diopters larger than the optical power of the main portion of oval lens body 12.

As can be further seen FIG. 1 an elastic ring 24 may run around the perimeter of oval lens body 12 to keep the lens body in the proper unfolded position. Also, haptic structures 26 may be affixed to oval lens body 12 or elastic perimeter ring 24 to hold IOL 10 in the proper position within a chamber of the human eye after insertion of the IOL into the eye.

Figure 2:
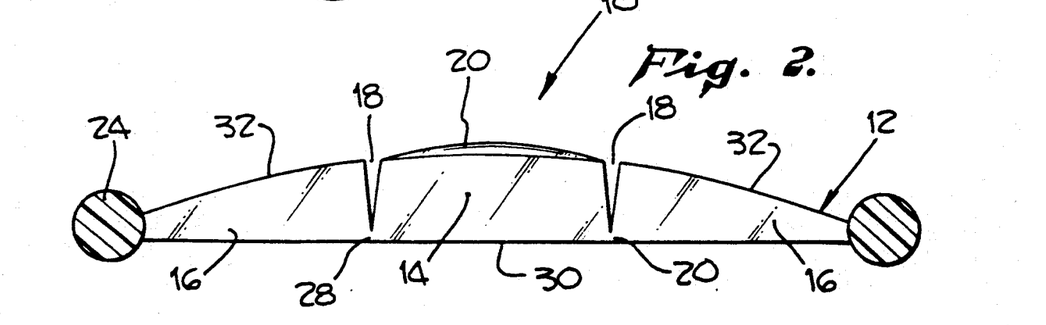
FIG. 2 is a cross-sectional view, taken along the lines 2—2 of FIG. 1, showing a foldable bifocal IOL in an unfolded position.
Figure 3:
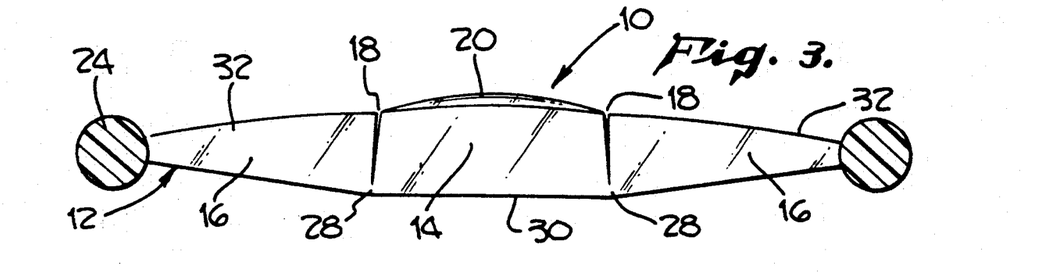
FIG. 3 is a cross-sectional view, taken along the lines 2—2 of FIG. 1, showing a foldable bifocal IOL in an overfolded position.
Figure 7:
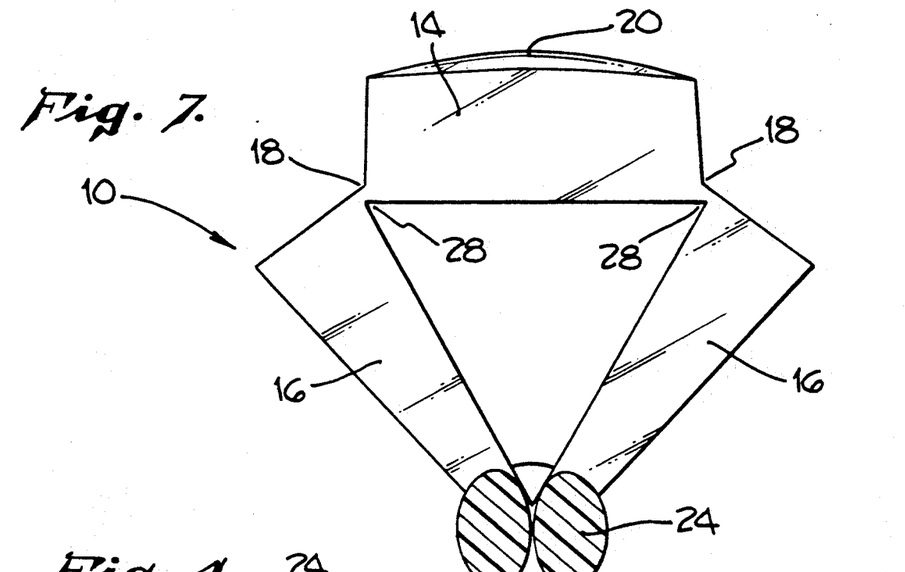
FIG. 7 is a cross-sectional view of a foldable bifocal IOL in a totally folded position.

Turning now to FIG. 7, there is depicted a cross-sectional view of a foldable bifocal IOL 10 in a fully folded position. Folding is achieved by bending side segments 16 away from central segment 14 as a result of separation cuts 18 made along oval lens body 12. As is seen in FIGS. 2, 3 and 7, separation cuts 18 in oval lens body 12 do not go completely through the lens body. Rather, the distance between the bottom 28 of cuts 18 and the lower surface 30 of oval lens body 12 is approximately 100 micrometers.

Turning now to FIG. 2, there is shown a foldable bifocal IOL in a nearly completely unfolded position. Cuts 18 separating central segment 14 from side segments 16 are wedge-shaped. For purposes of clarity, the size of cuts 18 and the wedged angle formed by the cuts are exaggerated. In reality, with oval lens body 12 in an unfolded position, cuts 18 will be only approximately 100 micrometers wide at their widest separation.

Turning now to FIG. 3, it is seen that the wedge-like nature of cuts 18 allow elastic perimeter ring 24 to pull side sections 16 into what is described as an "overfolded" position. Again, for purposes of clarity, the degree of over-folding is exaggerated. However, for any amount of over-folding, oval lens body 12 would have to stretch elastic perimeter ring 24 before the lens body could re-fold. Due to the absence of any significant forces on an IOL once it is implanted, re-folding cannot happen. Of course, since the upper surface 32 of oval lens body 12 is spherical in nature, the spherical surfaces of side segments 16 must be set at the proper angle to conform to the spherical surface of central segment 14 after over-folding has occured. This may be accomplished by the physician during the implantation process.

Figure 4:
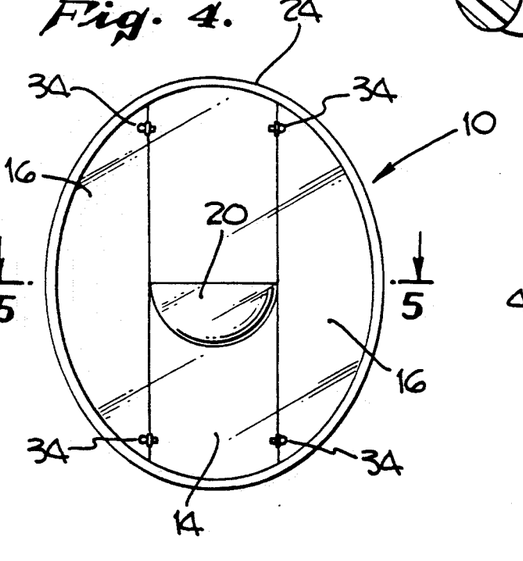
FIG. 4 is a partial top-plan view of another embodiment of a foldable bifocal IOL illustrating the principles of the present invention.
Figure 5:
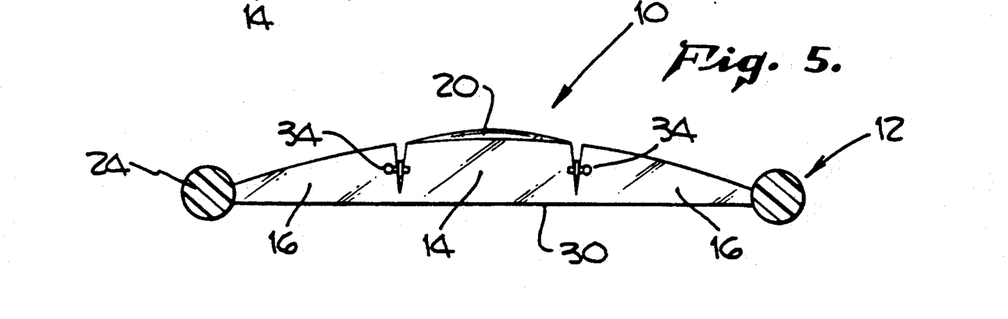
FIG. 5 is a cross-sectional view, taken along the lines 4—4 of FIG. 4, and showing a foldable bifocal IOL lens in an unfolded position.
Figure 6:
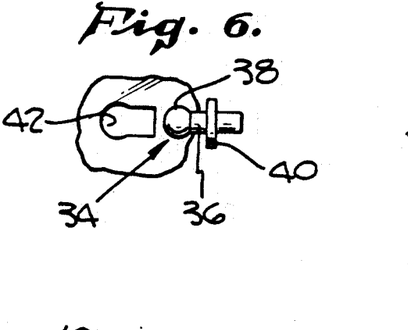
FIG. 6 is a side plan view of the locking pin assembly contemplated by the present invention.

Another embodiment of the present invention demonstrates a different method to guarantee proper alignment of the spherical surfaces of side segments 16 and central segment 14. As is best seen in FIGS. 4, 5 and 6, locking pin assemblies 34 are embedded at a plurality of locations in cuts 18 to prevent over-folding of oval lens body 12. Locking pin assemblies 34 include a pin 36 with a spherical tip 38 and a flange 40. The flange 40 has approximately the same thickness as the gap created by cuts 18. Locking pin assembly 34 also includes spherically ended cavities 42 in the portions of the walls of cuts 18 formed by side segments 16. In operation, upon unfolding of oval lens body 12, spherical tip 38 of pin 36 is forced into cavity 42 and locked into place upon reaching the spherically formed end of cavity 42. As is seen in FIG. 5, flange 40 prevents over-folding of oval lens body 12 thereby causing the spherical surfaces of side segments 16 to align properly with the spherical surface of central segment 14. It takes considerable force to insert spherical tip 38 into spherically shaped cavity 42 since some of the material of oval lens body 12 must be temporarily displaced. As is discussed in greater detail hereinbelow, this force is supplied from outside the eye via insertion instrument 44. Once spherical tip 38 is located in spherically ended cavity 42, oval lens body 12 is as rigid as it was prior to making separation cuts 18. Also, flanges 40 guarantee that side segments 16 and central segment 14 are in the proper position to avoid double images. Rotational misalignment of side segments 16 and central segment 14 is avoided because lower surface 30 of oval lens body 12 forms a type of diaphragm since separation cuts 18 were halted before breaking through lower surface 30. Although the mechanical strength of this diaphragm is marginal against tearing, it is sufficient to prevent rotation of side segments 16 and central segment 14 against one another. Further, as is discussed hereinbelow, the design of insertion instrument 44 prevents any shear stress which could induce tearing along separation cuts 18.

Figure 8:
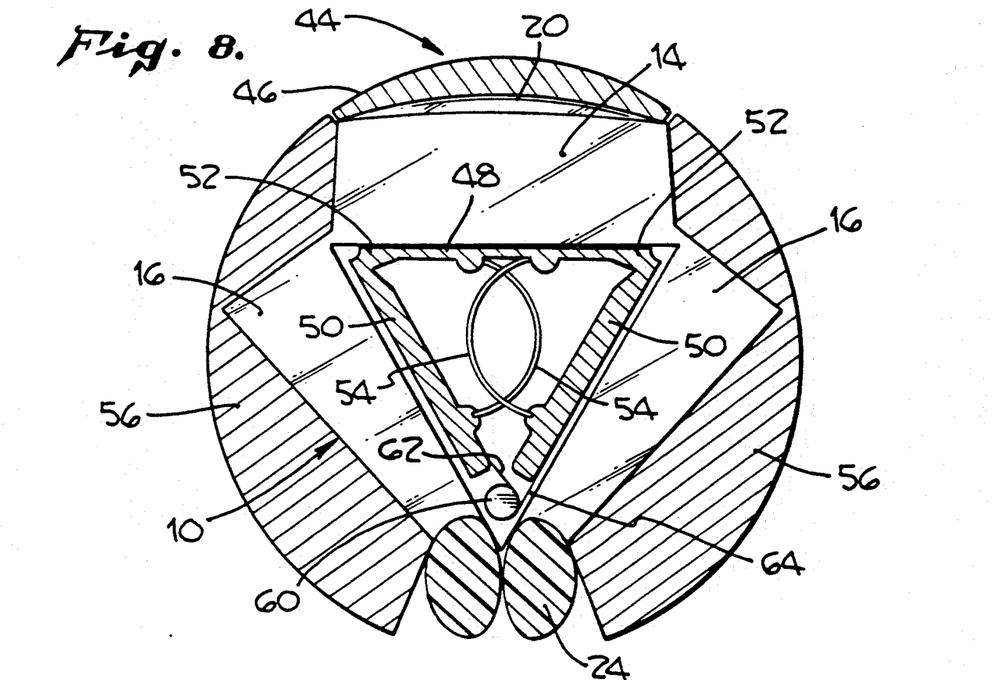
FIG. 8 is a cross-sectional view of a foldable bifocal IOL and IOL insertion instrument illustrating the principles of the present invention.
Figure 9:
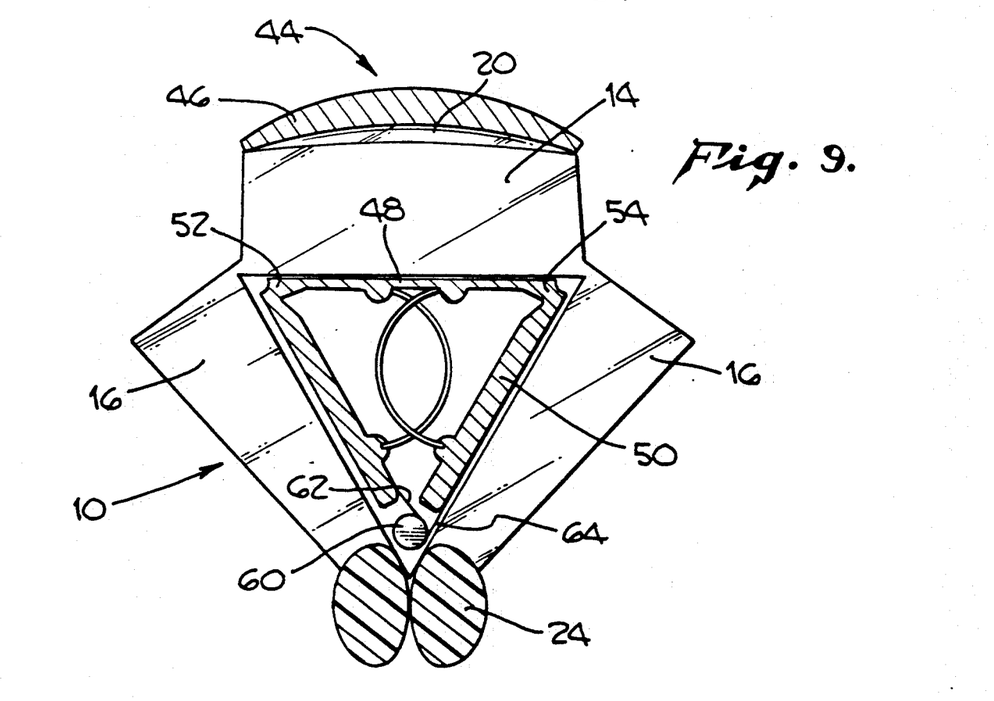
FIG. 9 is a cross-sectional view of a foldable bifocal IOL and IOL insertion instrument with the insertion instrument's tunnel shields withdrawn.
Figures 10, 11, 15:
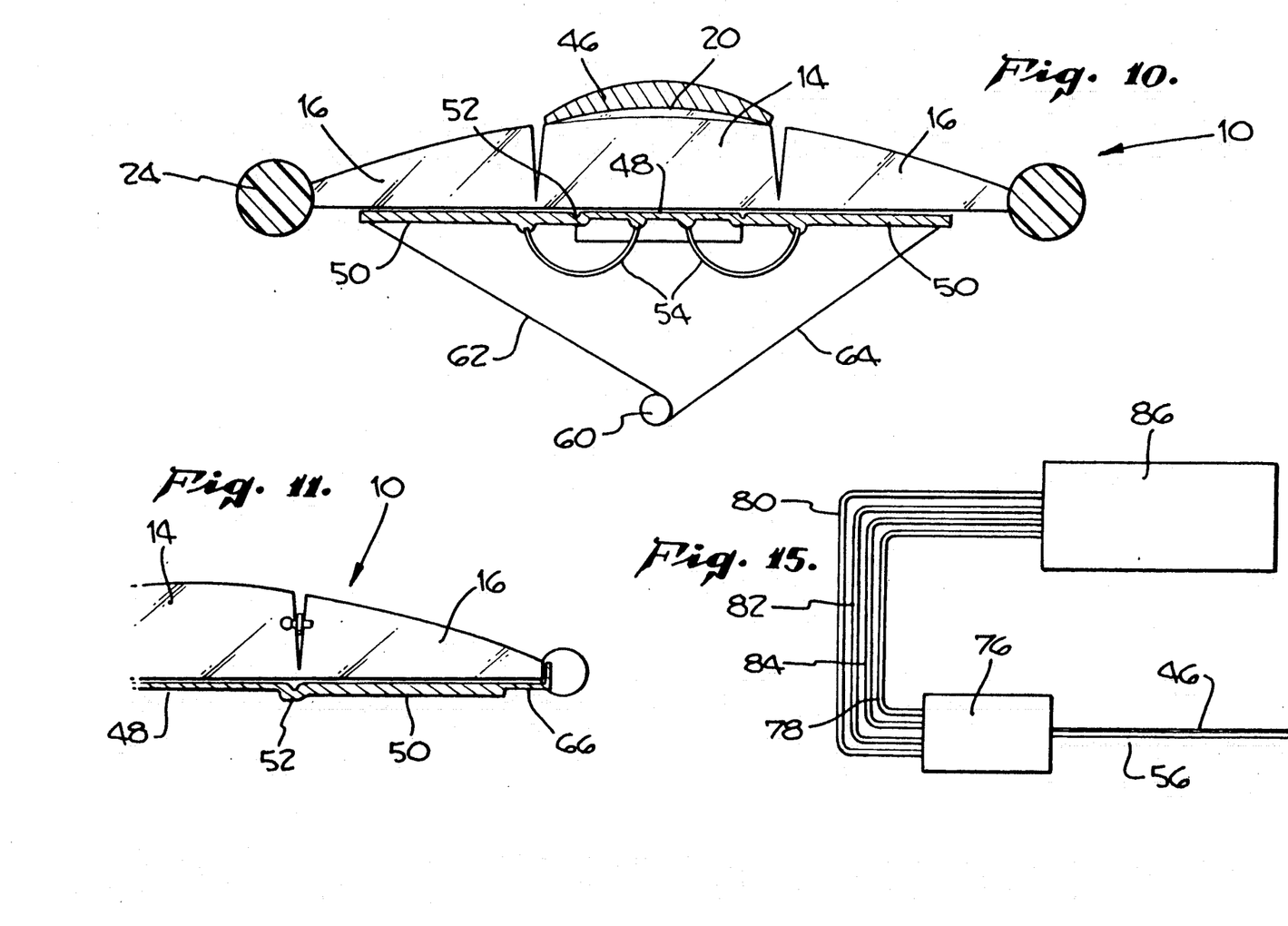
FIG. 10 is a cross-sectional view of a foldable bifocal IOL and IOL insertion instrument with the IOL in an unfolded position.
FIG. 11 is a partial cross-sectional view of an alternative embodiment of a foldable bifocal IOL showing a detail of the IOL's lock-in mechanism.
FIG. 15 is a schematic diagram of the automated insertion system contemplated by the present invention.
Figure 13:
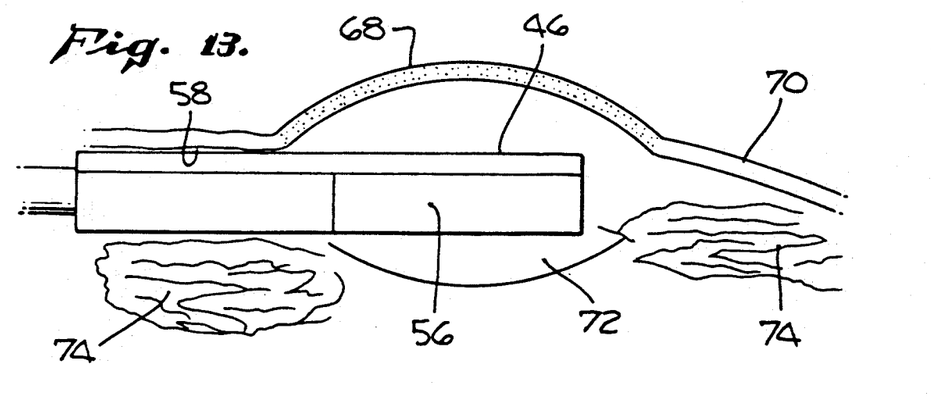
FIG. 13 is a cross-sectional view of part of a human eye showing an insertion instrument inserted in the eye.
Figure 14:
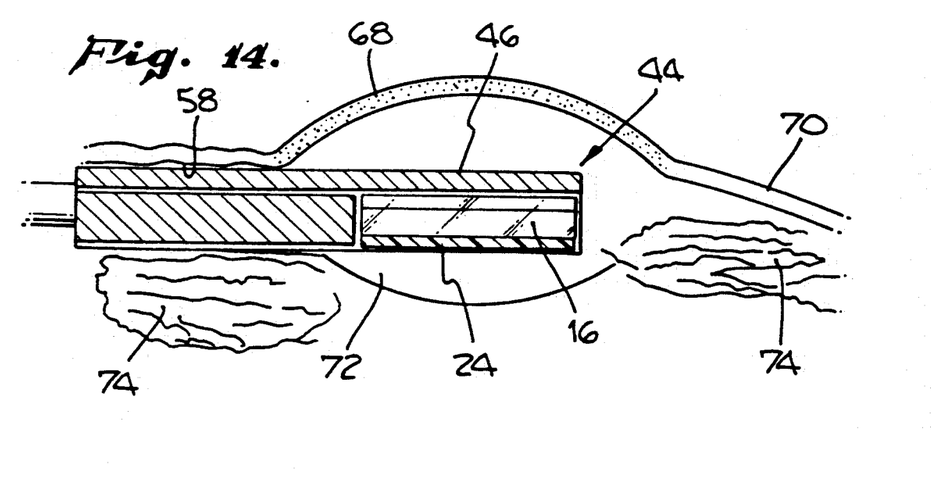
FIG. 14 is a cross-sectional view of part of a human eye with an insertion instrument inserted in the eye with its tunnel shields withdrawn.

Turning now to FIG. 8, it shows a foldable bifocal IOL in a completely folded position and held in this position by insertion instrument 44. Insertion instrument 44 includes top and bottom segments 46 and 48, which hold central segment 14 in a vise-like grip to provide a stable base against which side segments 16 can be unfolded. Unfolding is accomplished by platforms 50 with the aid of hinges 52 and unfolding springs 54. During its travel through insertion tunnel 58, foldable bifocal IOL 10 is protected by tunnel shields 56. FIG. 9 depicts insertion instrument 44 with tunnel shields 56 withdrawing. As is seen in FIGS. 13 and 14, tunnel shields 56 are withdrawn parallel to the axis of insertion tunnel 58. Also included in insertion instrument 44 is retaining drum 60, around which is wrapped strings 62 and 64. Unfolding of IOL 10 is accomplished by unfurling strings 62, 64 from around drum 60. Pushed by springs 54, platforms 50 will unfold and force IOL 10 into its unfolded position. The final unfolded position of IOL 10 is depicted in FIG. 10. If the embodiment involving locking pin assemblies 34 is used, springs 54 will force spherical tips 38 into their intended positions in spherically ended cavities 42. If locking pin assemblies are not used and over-folding is used, springs 54 will push platforms 50 so that side segments 16 go into an over-folded configuration.

In yet another embodiment, as seen in FIG. 11, when locking pin assemblies 34 are employed, shear stress to the uncut portions of separation cuts 18 may be avoided by hooks 66 affixed to the ends of platforms 50. Hooks 66 hold side segments 16 against central segment 14, thereby relieving the stress on the uncut portions of separation cuts 18 during and after the unfolding process.

Figure 12:
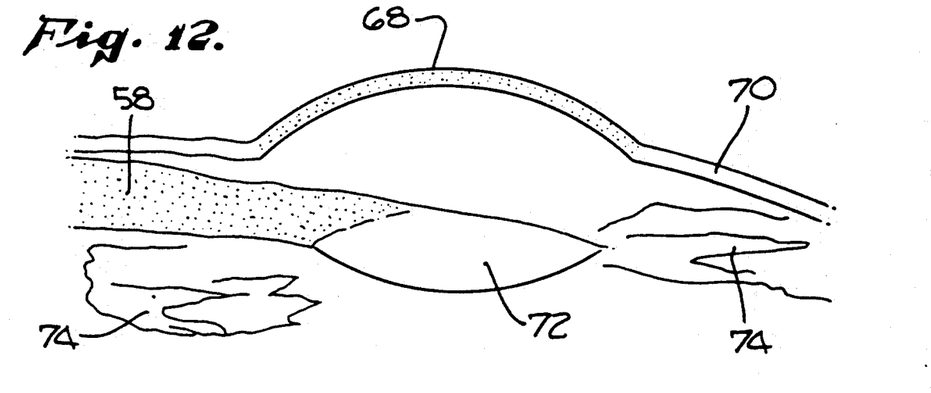
FIG. 12 is a cross-sectional top plan view of part of a human eye showing an IOL insertion tunnel.

Further understanding of the insertion procedure may be gained through an examination of FIG. 12 which depicts a cross-sectional top plan view of a portion of a human eye showing the cornea 68, the sclera 70, the human lens 72 and the zonule/ciliary muscle regions 74. As seen in FIGS. 13 and 14, insertion instrument 44 is inserted in the proper position in the eye through insertion tunnel 58. Tunnel shields 56 may then be withdrawn, exposing side segments 16 and elastic perimeter ring 24. Complete unfolding of IOL 10, as described hereinabove, may now proceed. After unfolding has proceeded, the grip exerted by top and bottom segments 46 and 48 is relaxed. Platforms 50 may be re-folded by refurling strings 62, 64 with the aid of drum 60. Insertion instrument 44 may now be used to move the unfolded and locked-in IOL 10 into its proper position if it is not already in such position. Once this is accomplished, insertion instrument 44 may be withdrawn.

FIG. 15 shows a block diagram of the combined foldable bifocal IOL and insertion instrument system. While the unfolding procedure and subsequent refolding of platforms 50 on insertion instrument 44 can be accomplished by hand controls operated by the surgeon, an alternative embodiment may be used where the unfolding procedure is automated. The procedure requires two rotary hydraulic actuators and two linear hydraulic actuators which are depicted as being located in actuator box 76. Each actuator is supplied by its separate flexible actuator hose 78, 80, 82 and 84. The flexible actuator hoses 78, 80, 82, 84 are connected to and controlled by a pressure source and controlled valve assembly 86. The pressure source and control valve assembly is an electromechanical device and is activated by signals controlled by a microprocessor, which is not shown. One of the rotary hydraulic actuators in actuator box 76 controls the grip of the vise formed by top and bottom segments 46 and 48 around central segment 14. The second rotary hydraulic actuator controls the unfurling and refurling of strings 62, 64 around drum 60. The two linear actuators in actuator box 76 may be used to withdraw tunnel shields 56. The hydraulic fluid used in connection with the hydraulic actuators is distilled water or a balanced saline solution. In this fashion, sterilization procedures are facilitated and, in case of an inadvertent leak of an actuator, no fluid that is incompatible with the eye is present.

It is to be understood that the foregoing description and accompanying drawings relate only to preferred embodiments of the present invention. Other embodiments may be utilized without departing from the spirit and scope of the invention. Accordingly, it is to be further understood that the description and drawings set forth hereinabove are for illustrative purposes only and do not constitute a limitation on the scope of the invention.

What is claimed is:

1. A foldable artificial intraocular lens for insertion into a human eye comprising:
   a foldable lens body divided into three zones by two separation cuts, said separation cuts being generally parallel to one another and extending substantially but not completely through said foldable lens body thereby facilitating unfolding of said foldable lens body along said separation cuts; and
   an elastic ring extending around the perimeter of said foldable lens body.

2. A foldable introcular lens as in claim 1 wherein said three zones further comprise two side zones and one center zone, said center zone having a centrally located first hemispherical segment having an optical power suitable for reading and the remainder of said foldable lens having an optical power suitable for far distance vision.

3. A foldable intraocular lens as in claim 2 wherein said center zone has a centrally located second hemispherical segment, not overlapping with said first hemispherical segment and having an optical power suitable for intermediate distance vision.

4. A foldable introcular lens as in claim 3 wherein the optical power of said first hemispherical segment is approximately 3.5 diopters greater than the optical power of the portion of said foldable lens having an optical power suitable for far distance vision and the optical power of said second hemispherical segment is at least approximately 1 diopter but less than approximately 2.5 diopters greater than the optical power of the portion of said foldable lens having an optical power suitable for far distance vision.

5. A foldable intraocular lens as in claim 2 wherein the optical power of said first hemispherical segment is approximately 3.5 diopters greater than the optical power of the remainder of said foldable lens.

6. A foldable intraocular lens as in claim 2 wherein said foldable lens is generally oval in shape having a long axis of approximately 6 mm and a short axis of approximately 5 mm and said separation cuts extend generally parallel to said long axis so that said side zones have a width along said short axis of approximately 1.5 mm and said center zone has a width along said short axis of approximately 2 mm.

7. A foldable intraocular lens as in claim 1 wherein the depth of said separation cuts is adjusted to leave uncut approximately 100 micrometers of said foldable lens.

8. A foldable intraocular lens as in claim 1 further comprising means for locking said foldable lens body in an unfolded position after insertion of said lens body into a human eye.

9. A foldable intraocular lens system as in claim 8 wherein said locking means comprises:
   a plurality of locking pins each having a first spherically-tipped end, a second end and a flange located between said first and second ends with said second ends being embedded in said separation cuts; and
   a plurality of spherically-ended locking pin receiving cavities embedded in said separation cuts and oriented so that said spherically-tipped first ends of said locking pins enter and engage said spherical ends of said receiving cavities when said foldable lens body is in an unfolded position.

10. A foldable intraocular lens system comprising:
    a foldable artificial lens implant divided into three zones by two separation cuts, said separation cuts being generally parallel to one another and extending substantially but not completely through said foldable implant thereby facilitating folding and unfolding of said foldable implant along said separation cuts;
    an elastic ring extending around the perimeter of said foldable lens implant; and
    a lens insertion instrument for inserting said foldable implant in a folded position into an eye, unfolding said foldable implant inside said eye and securing said unfolded implant at a proper location in said eye.

11. A foldable intraocular lens system as in claim 10 wherein said three zones further comprise two side zones and one center zone, said center zone having a centrally located first hemispherical segment having an optical power suitable for reading and the remainder of said foldable implant having an optical power suitable for far distance vision.

12. A foldable intraocular lens system as in claim 11 wherein said center zone has a centrally located second hemispherical segment, not overlapping with said first hemispherical segment and having an optical power suitable for intermediate distance vision.

13. A foldable intraocular lens system as in claim 11 wherein said foldable lens implant is generally oval in shape having a long axis of approximately 6 mm and a short axis of approximately 5 mm and said separation cuts extend generally parallel to said long axis so that said side zones have a width along said short axis of approximately 1.5 mm and said center zone has a width along said short axis of approximately 2 mm.

14. A foldable intraocular lens system as in claim 10 wherein said three zones further comprise two side zones and one center zone and said insertion instrument further comprises means for gripping said center zone and unfolding said side zones along said separation cuts.

15. A foldable intraocular lens system as in claim 14 wherein said gripping and unfolding means includes a top segment and a bottom segment oriented for gripping said center zone, two platforms rotatably affixed to said bottom segment and means for rotating said platforms against said side zones to force said side zones from a folded to an unfolded position.

16. A foldable intraocular lens system as in claim 15 wherein said rotating means includes unfolding springs for exerting force against said platforms to facilitate unfolding of said side zones and a drum and string assembly for controlling the rotational movement of said platforms acted upon by said springs and for rotating said platforms against the force of said springs after unfolding of said side zones is complete.

17. A foldable intraocular lens system as in claim 16 wherein said insertion instrument further comprises a plurality of removable tunnel shields for shielding said foldable implant during insertion into an eye.

18. A foldable intraocular lens system as in claim 17 wherein said drum and string assembly may be controlled by a plurality of electronically controlled hydraulic rotary actuators that may be used therewith and said tunnel shields may be removed from the eye by a plurality of electronically controlled hydraulic linear actuators that may be used therewith.

19. A foldable intraocular lens system as in claim 10 wherein said insertion instrument further comprises a plurality of removable tunnel shields for shielding said foldable implant during insertion into an eye.

20. A foldable intraocular lens as in claim 15 further comprising at lease one hook affixed to each of said platforms, said hooks constructed and arranged to grip said foldable intraocular lens and aid in the unfolding of said foldable intraocular lens after insertion in an eye.

21. A foldable intraocular lens system as in claim 10 further comprising means for locking said foldable implant in an unfolded position after insertion of said implant into an eye.

22. A foldable intraocular lens system as in claim 21 wherein said locking means comprises:

a plurality of locking pins having a first spherically-tipped end, a second end and a flange located between said first and second ends with said second ends being embedded in said separation cuts; and a plurality of spherically-ended locking pin receiving cavities embedded in said separation cuts and oriented so that said spherically tipped first ends of said locking pins enter and engage said spherical ends of said receiving cavities when said foldable lens body is in an unfolded position.

23. A foldable intraocular lens insertion instrument comprising:

a top segment and a bottom segment constructed and arranged for gripping a foldable intraocular lens in a vise-like grip;

two platforms rotatably affixed to said bottom segment; and means for controlling the rotation of said platforms whereby unfolding of said foldable intraocular lens is facilitated.

24. A foldable intraocular lens insertion instrument as in claim 23 wherein said means for controlling rotation includes unfolding springs for exerting force against said platforms to facilitate unfolding of said foldable intraocular lens.

25. A foldable intraocular lens insertion instrument as in claim 24 wherein said means for controlling rotation further comprises a retainer drum and string assembly with said assembly having at least one string operationally connected to each of said platforms and said strings arranged to be windable and unwindable about said drum to control the rotational movement of said platforms acted upon by said springs and to aid in rotating said platforms against the force of said springs after unfolding of said foldable intraocular lens is complete.

26. A foldable intraocular lens insertion instrument as in claim 25 wherein said insertion instrument includes a plurality of removable tunnel shields for shielding said foldable intraocular lens during insertion into an eye.

27. A foldable intraocular lens insertion instrument as in claim 26 wherein said drum and string assembly may be controlled by a plurality of electronically controlled hydraulic rotary actuators that may be used therewith and said tunnel shields may be removed from the eye by a plurality of electronically controlled hydraulic linear actuators that may be used therewith.

28. A foldable intraocular lens insertion instrument as in claim 23 further comprising at least one hook affixed to each of said platforms, said hooks constructed and arranged to grip said foldable intraocular lens and aid in the unfolding of said foldable intraocular lens after insertion in an eye.

* * * * *